United States Patent [19]

Addor et al.

[11] Patent Number: 5,237,099

[45] Date of Patent: Aug. 17, 1993

[54] INSECTICIDAL SUBSTITUTED AND UNSUBSTITUTED BENZOIC ACID 1-ALKYL, 2-ALKYL AND 2-CYCLOALKYLHYDRAZIDES

[75] Inventors: Roger W. Addor, Pennington, N.J.; David G. Kuhn, Newton, Pa.; Donald P. Wright, Jr., Pennington, N.J.

[73] Assignee: American Cyanamid Company, Stamford, Conn.

[21] Appl. No.: 829,517

[22] Filed: Jun. 8, 1990

Related U.S. Application Data

[60] Continuation of Ser. No. 298,713, Jan. 19, 1989, which is a division of Ser. No. 926,780, Nov. 12, 1986, Pat. No. 4,814,349, which is a continuation-in-part of Ser. No. 806,981, Dec. 9, 1985, abandoned.

[51] Int. Cl.$^5$ .......................................... C07C 109/10
[52] U.S. Cl. .................................. 564/149; 564/150; 560/13; 560/18; 560/22; 560/37; 560/42; 558/413; 558/415; 558/416
[58] Field of Search ............... 560/13, 18, 22, 37, 560/42; 564/149, 150; 538/413, 415, 416

[56] References Cited

U.S. PATENT DOCUMENTS 3,855,289  12/1974  Alt .................................... 564/149

OTHER PUBLICATIONS

Baumgarten et al., J. Org. Chem., 41(24), 3805 (1976).
CA 71(21):10144r (Chem. Ber., 102(9), 2889-99), 1971.
Preparation of Alkyl Azides from Hydrazine Derivatives, Journal of Organic Chemistry, Smith, A. S. et al., vol. 23, No. 11 (1958) pp. 1595-1599.

Primary Examiner—Nicky Chan
Attorney, Agent, or Firm—Michael P. Morris

[57] ABSTRACT

The present invention relates to methods for controlling insect populations and for protecting living plants from insect attack by applying to said plants or to the soil in which they are growing an insecticidally-effective amount of a substituted benzoic acid 1 or 2-alkyl or 2-cycloalkylhydrazide.

Novel substituted benzoic acid 1 and 2-alkyl and 2-cycloalkylhydrazides effective as insecticides or intermediates for the preparation of insecticidal diacylhydrazides also are presented.

4 Claims, No Drawings

INSECTICIDAL SUBSTITUTED AND UNSUBSTITUTED BENZOIC ACID 1-ALKYL, 2-ALKYL AND 2-CYCLOALKYLHYDRAZIDES

BACKGROUND OF THE INVENTION

This application is a continuation of U.S. application Ser. No. 298,713, filed Jan. 19, 1989, now abandoned, which is a divisional of U.S. application Ser. No. 926,780, filed Nov. 12, 1986, now U.S. Pat. No. 4,814,349, which is a continuation-in-part of U.S. Pat. application Ser. No. 806,981 filed Dec. 9, 1985, now abandoned.

The present invention relates to compounds which are useful intermediates in the processing of dibenzoylhydrazines. These dibenzoylhydrazines are effective insecticidal stomach poisons and also are effective systemically in protecting living plants.

Further, the compounds of the invention are effective as insecticides themselves. These novel compounds and others have been found to control insects and protect living plants from insect attack.

Thus, it is an object of the present invention to provide these methods for controlling insect pests and protecting living plants through an extended period of active growth from insects which infest said living plants.

It is another object of the invention to provide novel substituted benzoic acid 1-alkyl-, 2-alkyl- and 2-cycloalkylhydrazides, preferably 1 or 2-tert-butylhydrazides, as insecticides and also to provide many of said compounds useful in the preparation of dibenzoylhydrazine insecticides.

These and further objects of the invention will become apparent by the following more detailed description of the invention.

SUMMARY OF THE INVENTION

The present invention relates to a method for controlling insects and protecting living plants from insect attack by applying to the food supply of said insects, including living plants upon which said insects feed, or the insects' breeding grounds or habitat, an insecticidally-effective amount of a compound depicted by formula (I):

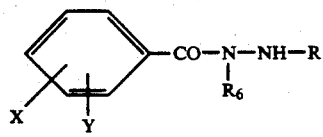
(I)

wherein R and $R_6$ are each independently hydrogen, $C_2$–$C_6$ alkyl or $C_5$–$C_6$ cycloalkyl; X and Y are each independently H, $C_1$–$C_3$ alkyl, $C_1$–$C_3$ alkoxy, $C_1$–$C_3$ alkylthio, $C_1$–$C_3$ alkylsulfinyl, $C_1$–$C_3$ alkylsulfonyl, cyano, F, Cl, Br, I, nitro, $CF_3$, $R_1CF_2Z$—, 1,1-difluoro-2,2-dichloroethoxy, $R_2CO$ or $R_3R_4N$ and when taken together X and Y may form a ring in which XY are represented by the structure:

 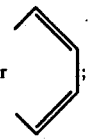

Z is $S(O)n$ or O; $R_1$ is H, F, $CHF_2$, $CHFCl$ or $CF_3$; $R_2$ is $C_1$–$C_3$ alkyl, $C_1$–$C_3$ alkoxy or $R_3R_4N$; $R_3$ is H or $C_1C_3$ alkyl; $R_4$ is H, $C_1$–$C_3$ alkyl or $R_5CO$; $R_5$ is H or $C_1$–$C_3$ alkyl and n is 0, 1 or 2; with the provisos that when R is hydrogen, $R_6$ is $C_2$–$C_5$ alkyl or $C_5$–$C_6$ cycloalkyl and when $R_6$ is hydrogen, R is $C_2$–$C_5$ alkyl or $C_5$–$C_6$ cycloalkyl.

A preferred group of compounds of the present invention include formula (I) compounds wherein R is tert-butyl, $R_6$ is hydrogen and X and Y are as described hereinabove.

Another group of preferred compounds of the present invention include formula (I) compounds wherein R is hydrogen, $R_6$ is tert-butyl and X and Y are as described hereinabove.

The present invention also relates to novel substituted benzoic acid 1-alkyl-, 2-alkyl- and 2-cycloalkylhydrazides, effective as insecticides, having the structure depicted by formula (II):

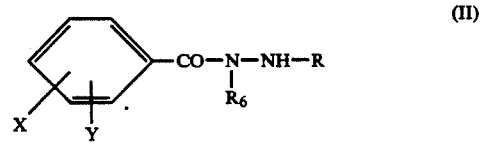
(II)

wherein R and $R_6$ are each independently hydrogen, $C_2$–$C_6$ alkyl or $C_5$–$C_6$ cycloalkyl; X and Y are each independently H, $C_1$–$C_3$ alkyl, $C_1$–$C_3$ alkoxy, $C_1$–$C_3$ alkylthio, $C_1$–$C_3$ alkylsulfinyl, $C_1$–$C_3$ alkylsulfonyl, cyano, F, Cl, Br, I, nitro, $CF_3$, $R_1CF_2Z$—, 1,1-difluoro-2,2-dichloroethoxy, $R_2CO$ or $R_3R_4N$ and when taken together X and Y may form a ring in which XY are represented by the structure:

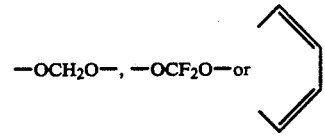 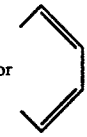

Z is $S(O)n$ or O; $R_1$ is H, F, $CHF_2$, $CHFCl$ or $CF_3$; $R_2$ is $C_1$–$C_3$ alkyl, $C_1$–$C_3$ alkoxy or $R_3R_4N$; $R_3$ is H or $C_1$–$C_3$ alkyl; $R_4$ is H, $C_1$–$C_3$ alkyl or $R_5CO$; $R_5$ is H or $C_1$–$C_3$ alkyl and n is 0, 1 or 2; with the provisos that when R is hydrogen, $R_6$ is $C_2$–$C_5$ alkyl or $C_5$–$C_6$ cycloalkyl and when $R_6$ is hydrogen, R is $C_2$–$C_5$ alkyl or $C_5$–$C_6$ cycloalkyl; and provided also that when R is tert-butyl and Y is chloro in the para position of the ring, X is a substituent other then hydrogen.

The novel substituted formula (II) benzoic acid 1-alkyl-, 2-alkyl- and 2-cycloalkylhydrazides, like the formula (I), 1-alkyl-, 2-alkyl- and 2-cycloalkylhydrazides, are potent stomach poisons. As such, these formula (I) and formula (II) hydrazides effectively control insect populations and protect plants from insect attack. Insecticidally-effective amounts of the active compound can be applied to the foliage of plants upon which the insects feed or to the soil, water or other media in which said plants are growing. These compounds may also be made available to the insects in the form of baits or applied to the insects' breeding grounds and habitat.

Additionally, many of the novel formula (II) benzoic acid 1-alkyl-, 2-alkyl- and 2-cycloalkylhydrazides, substituted with halogen, $CH_3$, $CF_3$, $-OCH_3$, $-OCH_2O-$, $OCF_2O-$, $NH_2$, $NO_2$ or $-CH=CH-CH=CH-$, are useful as intermediates for the preparation of dibenzoylhydrazines which are effective as insecticidal agents and systemic soil insecticidal agents.

DETAILED DESCRIPTION OF THE INVENTION

Process of Manufacture

The formula (I) benzoic acid 1-alkyl-, 2-alkyl- and 2-cycloalkylhydrazides of the present invention are depicted by the following structure:

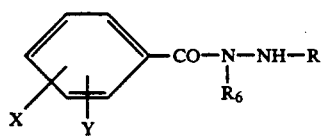
(I)

wherein R and $R_6$ are each independently hydrogen, $C_2$-$C_6$ alkyl or $C_5$-$C_6$ cycloalkyl; X and Y are each independently H, $C_1$-$C_3$ alkyl, $C_1$-$C_3$ alkoxy, $C_1$-$C_3$ alkylthio, $C_1$-$C_3$ alkylsulfinyl, $C_1$-$C_3$ alkylsulfonyl, cyano, F, Cl, Br, I, nitro, $CF_3$, $R_1CF_2Z-$, 1,1-difluoro-2,2-dichloroethoxy, $R_2CO$ or $R_3R_4N$ and when taken together X and Y may form a ring in which XY are represented by the structure:

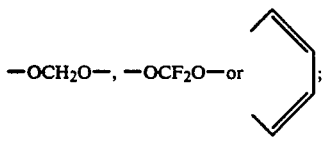

Z is $S(O)n$ or O; $R_1$ is H, F, $CHF_2$, CHFCl or $CF_3$; $R_2$ is $C_1$-$C_3$ alkyl, $C_1$-$C_3$ alkoxy or $R_3R_4N$; $R_3$ is H or $C_1$-$C_3$ alkyl; $R_4$ is H, $C_1$-$C_3$ alkyl or $R_5CO$; $R_5$ is H or $C_1$-$C_3$ alkyl and n is 0, 1 or 2; with the provisos that when R is hydrogen, $R_2$ is $C_2$-$C_5$ alkyl or $C_5$-$C_6$ cycloalkyl and when $R_6$ is hydrogen, R is $C_2$-$C_5$ alkyl or $C_5$-$C_6$ cycloalkyl.

The formula (I) 2-alkyl- and 2-cycloalkylhydrazides of the invention are prepared by reacting an alkyl- or cycloalkylhydrazine hydrohalide with a benzoylhalide in the presence of aqueous base.

Generally, the alkyl or cycloalkylhydrazine hydrohalide is dispersed in an organic solvent, such as methylene chloride, ether or the like, and the resulting mixture then admixed with aqueous base. Usually, about two to six molar equivalents of base, such as sodium carbonate or sodium hydroxide, per equivalent of alkylhydrazine hydrohalide are used to achieve the benzoylation of the alkyl hydrazine. The thus-prepared mixture is then admixed with the appropriate benzoyl halide dissolved or dispersed in an organic solvent, preferably the same solvent used for dissolution of the alkyl- or cycloalkylhydrazine hydrohalide.

The mixture is stirred or agitated for a sufficient period of time to form the benzoic acid alkyl- cycloalkylhydrazide which is readily recovered from the mixture by separation of the aqueous phase from the organic phase and evaporation of the organic solvent from said organic phase.

The reaction is graphically illustrated below:

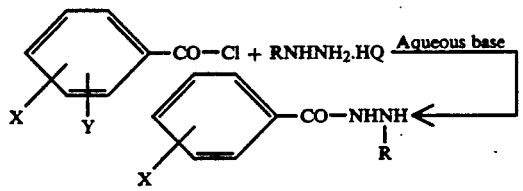

wherein Q is halogen, preferably chlorine and R, X and Y are as described for formula (I) compounds illustrated hereinabove.

The formula (I) benzoic acid, 1-alkyl and 2-cycloalkylhydrazides of this invention, depicted by the structure:

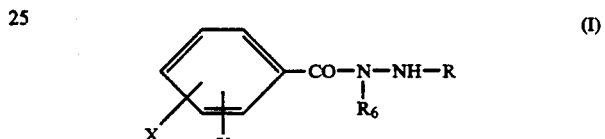
(I)

wherein R is hydrogen; $R_6$ is $C_2$-$C_6$ alkyl or $C_5$-$C_6$ cycloalkyl and X and Y are as described hereinabove, are prepared by reacting an alkylhydrazine or cycloalkylhydrazine with acetone. After the mixture is permitted to stand for a short period of time, it is treated with ether and potassium hydroxide pellets. The ether layer is separated from the mixture and evaporated to yield the 1-alkyl-2-isopropylidenehydrazide or 1-cycloalkyl-2-isopropylidenehydrazide.

The resulting 1-alkyl- or 1-cycloalkyl-2-isopropylidene hydrazide then is reacted with a benzoyl halide in the presence of 10% sodium hydroxide to yield 1-alkyl or 1-cycloalkyl 2-isopropylidenehydrazide of benzoic acid. Hydrolysis of the thus-formed product with a dilute mineral acid such as 10% HCl in the presence of alcohol yields the 1-alkyl or 1-cycloalkylhydrazide of benzoic acid.

These reactions are illustrated as follows:

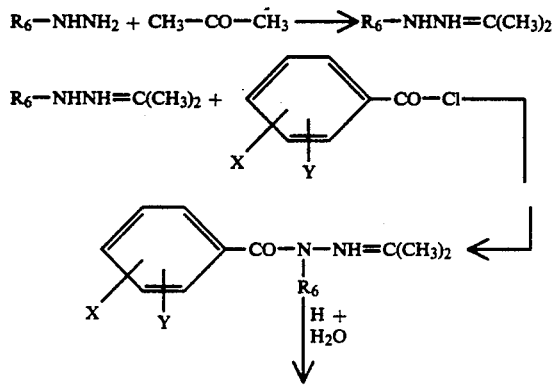

-continued

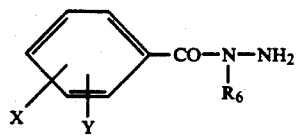

wherein $R_6$, X and Y are as described hereinabove.

Preparation of the formula (I) benzoic acid alkyl- and cycloalkylhydrazides of this invention, wherein $R_6$ is hydrogen, also is achieved by reduction of the appropriate benzoic acid alkylidene hydrazide with hydrogen in the presence of a noble metal catalyst, such as platinum or palladium. The reaction preferably is conducted in the presence of a lower alkyl ($C_1$–$C_4$) alcohol under a blanket of hydrogen maintained at about 20 to 60 psig. The reaction is illustrated below:

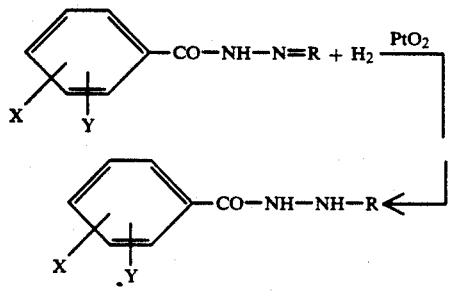

wherein $R_1$, X and Y are as described for formula (I) compounds hereinabove.

Formula (I) benzoic acid 2-alkylhydrazides and 2-cycloalkylhydrazides are useful as intermediates for the preparation of dibenzoylhydrazine compounds illustrated by formula (III), which are found to be extremely potent insect stomach poisons and systemic insecticidal agents. These dibenzoylhydrazines are effective for controlling a variety of insects including, but not limited to Lepidoptera, Homoptera, Orthoptera, Coleoptera and Diptera, and are likewise effective for protecting a variety of crops from insect attack.

The formula (III) dibenzoylhydrazine compounds have the following structure:

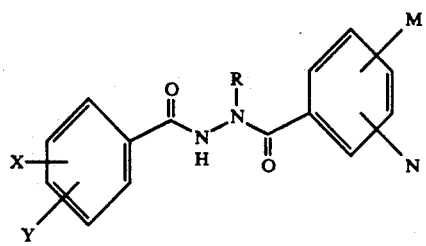

wherein R is $C_2$–$C_6$ alkyl or $C_5$–$C_6$ cycloalkyl; X, Y, M and N are each independently H, $C_1$–$C_3$ alkyl, $C_1$–$C_3$ alkoxy, $C_1$–$C_3$ alkylthio, $C_1$–$C_3$ alkylsulfinyl, $C_1$–$C_3$ alkylsulfonyl, cyano, F, Cl, Br, I, nitro, $CF_3$ or $R_1CF_2Z-$, 1,1-difluoro-2,2-dichloroethoxy, $R_2CO$ or $R_3R_4N$, and when taken together, X and Y may form a ring in which XY are represented by the structure:

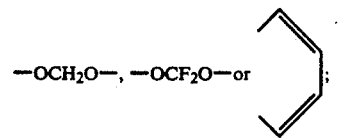

and when taken together, M and N may form a ring in which MN are represented by the structure:

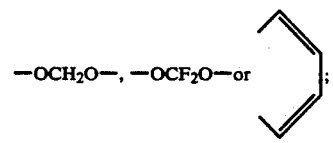

Z is $S(O)n$ or O; $R_1$ is H, F, $CHF_2$, CHFCl or $CF_3$; $R_2$ is $C_1$–$C_3$ alkyl, $C_1$–$C_3$ alkoxy or $R_3R_4N$; $R_3$ is H or $C_1$–$C_3$ alkyl; $R_4$ is H, $C_1$–$C_3$ alkyl or $R_5CO$; $R_5$ is H or $C_1$–$C_3$ alkyl and n is 0, 1 or 2; with the provisos that at least one of X, Y, M or N is a substituent other than hydrogen and when M is para nitro, at least one other of X, Y, or N must be a substituent other then hydrogen.

These formula (III) compounds are prepared by the reacting approximately equimolar amounts of a benzoic acid alkylhydrazide and a benzoyl halide in the presence of an aprotic solvent, such as an ether, chlorinated hydrocarbon or the like and aqueous base. Generally, about two to six molar equivalents of base per equivalent of benzoic acid alkylhydrazide are sufficient to bring the reaction to completion. The reaction is graphically illustrated below:

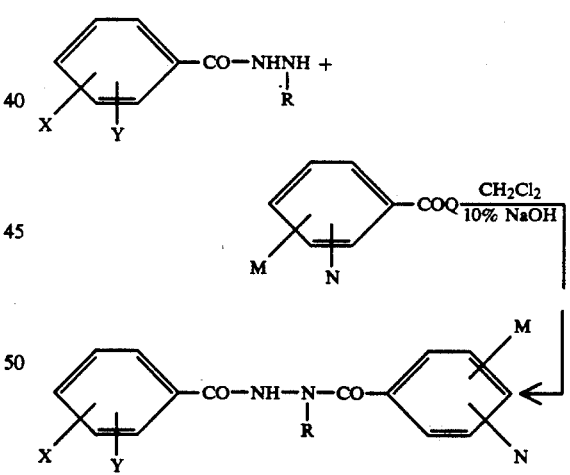

wherein Q is halogen; and R, X, Y, M and N are as described hereinabove for formula (III).

FORMULATIONS

The formula (I) and formula (II) benzoic acid 2-alkyl- and 2-cycloalkylhydrazides may be prepared and utilized as solid or liquid formulations.

In practice, protection of living plants is achieved by applying to the foliage of said plants and/or to the soil, water or other media in which they are growing, about 0.1 kg/hectare to about 10.0 kg/hectare, preferably about 0.28 to 4.0 kg/hectare, of the formula (I) or formula (II) benzoic acid 2-alkyl- or 2-cycloalkylhydrazide. Advantageously, application of these formulations to the insects habitat, food supply and/or breeding grounds at the above said rates also provide control of insect populations in the treated area.

If the active formula (I) or formula (II) compound is applied as a dilute spray, said spray should contain 10 ppm to about 10,000 ppm of the active ingredient to provide the desired protection and insect control.

A typical emulsifiable concentrate formulation is prepared by dispersing about 30% w/v of the benzoic acid 1-alkyl-, 2-alkyl and 2-cycloalkylhydrazide of the invention in 50% w/v of 2-pyrrolidone; in 10% w/v of n-butanol; 7% w/v of a polyalkylene glycol ether, such as POLYFAR® S320 manufactured by Westvaco-Polychemicals, Charleston Heights, S.C.; and 3.0% w/v of nonylphenoxy polyethoxy ethanol offered by Rohm and Haas Co as TRITON® N101.

Emulsifiable concentrates are especially useful for distributing the active benzoic acid 1-alkyl, 2-alkyl and 2-cycloalkylhydrazides of this invention since they are readily dispersed in water for application as liquid sprays. Such emulsifiable concentrates also may be added to irrigation water or flooded paddies, such as used for rice cultivation, or they may be applied directly to the plants or the locus to be protected from insect infestation using aerial applicators or ground equipment designed for ultra low volume (ULV) or low volume (LV) application of the undiluted concentrates as finely divided discrete droplets.

Granular formulations may be prepared by dissolving the active formula (I) or formula (II) hydrazide in a low-boiling solvent, such as methylene chloride, and spraying the thus-prepared solution on a sorptive carrier such as kaolin, bentonite, attapulgite, montmorillonite or the like, in sufficient amount to provide from about 2% to 20%, preferably about 3% to 15%, by weight of active ingredient based on the total weight of the granulated product.

Wettable powder formulations can be prepared by grinding together about 30% to 75% by weight of the active formula (I) or (II) hydrazide with about 5% to 10% by weight of an anionic surfactant, such as a naphthalene sulfonate condensate or a sodium or ammonium salt of a condensed mono naphthalene sulfonic acid; about 3% to 5% by weight of an anionic surfactant such as an alkyl naphthalene sulfonate, i.e. sodium di-n-butyl naphthalene sulfonate, sodium diisopropyl naphthalene sulfonate or the like; and the remainder of the composition an inert diluent such as attapulgite, kaolin, montmorillonite, talc, diatomaceous earth or the like.

The following examples are presented herein simply as illustrations of the present invention and are not limitative thereof.

EXAMPLE 1

Preparation of benzoic acid, 2-tert-butylhydrazide tert-Butylhydrazine hydrochloride (15.6 g, 0.125 mole) is dissolved in 350 mL of methylene chloride. To this solution is added 240 mL of 10% aqueous sodium hydroxide (24 g, 0.60 mole). A solution of benzoyl chloride (d=1.211, 14.5 mL, 17.6 g, 0.125 mole) in methylene chloride is then added at moderate rate to the rapidly stirring two-phase system.

After stirring the mixture for 24 hours at ambient temperatures, the methylene chloride phase is removed, washed with 5% aqueous sodium hydroxide, water, saturated sodium chloride solution, and then dried over sodium sulfate. Evaporation in vacuo gives 19.3 g of white solid, mp 87°–94° C., which is recrystallized from 2-propanol-water to give 13.0 g of product, mp 92°–94° C.

Substituting p-chlorobenzoyl chloride for benzoyl chloride in the above reaction yields p-chlorobenzoic acid, 2-tert-butylhydrazide; melting point 116°–122° C. Similarly, substituting p-fluorobenzoyl chloride, p-nitro- benzoyl chloride, o-toluyl chloride, m-fluorobenzoyl chloride, p-bromobenzoyl chloride, p-trifluoromethylbenzoyl chloride, o-anisyl chloride, p-toluyl chloride, o-chlorobenzoyl chloride, p-iodobenzoyl chloride, o-iodobenzoyl chloride, p-ethylbenzoyl chloride and o-fluorobenzoyl chloride, o-nitrobenzoyl chloride, for benzoyl chloride, yields respectively: p-fluorobenzoic acid, o-bromobenzoyl chloride, 2-tert-butylhydrazide; mp 136°–138° C.; p-nitrobenzoic acid, 2-tert-butylhydrazide; o-toluic acid, 2-tert-butylhydrazide; m-fluorobenzoic acid, 2-tert-butylhydrazide, mp 119°–120° C.; p-bromobenzoic acid, 2-tert-butylhydrazide; p-trifluoromethylbenzoic acid, 2-tert-butylhydrazide; anisic acid, 2-tert-butylhydrazide; p-toluic acid, 2-tert-butylhydrazide; o-chlorobenzoic acid, 2-tert-butylhydrazide; mp 68°–70° C.; o-iodobenzoic acid, 2-tert-butylhydrazide; p-ethylbenzoic acid, 2-tert-butylhydrazide; and o-fluorobenzoic acid, 2-tert-butylhydrazide; mp 58°–59° C.; o-nitrobenzoic acid, 2-tert-butylhydrazide; mp 116°–118° C.; o-bromobenzoic acid, 2-tert-butylhydrazide; mp 85°–87° C.; and N-methylanthranilic acid, 2-tert-butylhydrazide, mp 125°–129° C.

The above reactions are illustrated below:

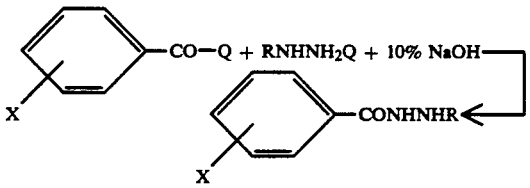

wherein Q is halogen, preferably chlorine; R is tert-butyl or tert-amyl. Other compounds that can be prepared by the above procedure using the appropriately substituted benzoyl halide include: m-chlorobenzoic acid, 2-tert-butylhydrazide, mp 120°–123° C.; p-cyanobenzoic acid, 2-tert-butylhydrazide, mp 135°–136° C.; anthranilic acid, 2-tert-butylhydrazide, mp 165°–167° C.; tert-butyl or isopropyl; and X is hydrogen, halogen, $C_1$–$C_3$ alkyl, methoxy, methylamino, $NH_2$, nitro or $CF_3$.

EXAMPLE 2

Preparation of 3,4-dichlorobenzoic acid, 2-tert-butylhydrazide

Tert-butylhydrazine hydrochloride (12.4 g, 0.1 mole) is added to a solution of sodium carbonate (23.3 g, 0.22 mole) in 100 mL of water and 250 mL of ether. A solution of 3,4-dichlorobenzoyl chloride (20.9 g, 0.1 mole) in 50 mL of ether is then added dropwise at 0°–15° C. After one hour, the reaction mixture is filtered and the filtrate is separated. The organic layer is washed with 100 mL of water, dried over anhydrous $MgSO_4$, filtered and evaporated. Recrystallization of the residue from 2-propanol gives white crystals: yield 6.4 g, mp 144°–145° C.

Following the above procedure, but substituting 2,4-dichlorobenzoyl chloride or 2,6-dichlorobenzoyl chloride for 3,4-dichlorobenzoyl chloride, yields, respectively 2,4-dichlorobenzoic acid, 2-tert-butylhydrazide, mp 115°–117° C. and 2,6-dichlorobenzoic acid, 2-tert-butylhydrazide, mp 173°–174° C.

Similarly, substituting 2-chloro-4-nitrobenzoyl chloride, 3-bromo-4-methylbenzoyl chloride, 2,6-difluorobenzoyl chloride, 2,5-dichlorobenzoyl chloride, 3,5-dichlorobenzoyl chloride or naphthoyl chloride, for 3,4-dichlorobenzoyl chloride, yields respectively: 2-chloro-4-nitrobenzoic acid, 2-(tert)-butylhydrazide; 3-bromo-4-methylbenzoic acid, 2-(tert)-butylhydrazide; mp 95°–97° C.; 2,5-dichlorobenzoic acid, 2-(tert)-butylhydrazide and 3,5-dichlorobenzoic acid, 2-(tert)-butylhydrazide, mp 163°–165° C.; 1-naphthoic acid, 2-(tert)-butylhydrazide mp 148°–150° C.

These reactions are illustrated below:

$(CH_3)_3CNHNH_2 \cdot HCl \; +$

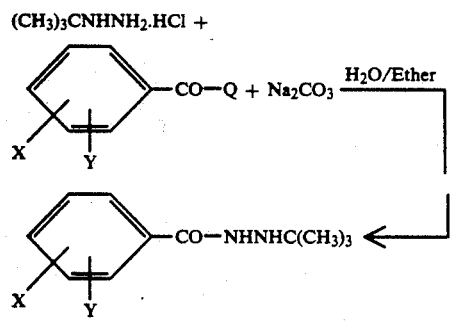

wherein Q is halogen, preferably chlorine; X and Y are each independently halogen, $C_1$–$C_3$ alkyl, methoxy, nitro or $CF_3$ and when taken together XY may represent

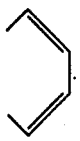

EXAMPLE 3

Preparation of 1,2-dibenzoyl-1-tert-butylhydrazine t-Butylhydrazine hydrochloride (101 g, 0.81 mole) is dissolved in 970 mL of 10% sodium hydroxide (97 g, 2.4 mole) in a three-liter flask with mechanical stirring. After addition of one liter of ether, the flask is fitted with a condenser and addition funnel.

Benzoyl chloride (176 mL, 213 g, 1.52 mole) in 70 mL of ether is then added over about a one hour period. The reaction proceeds exothermically with formation of a white solid. After stirring overnight, the mixture is filtered and the resulting solids dried and then recrystallized from isopropyl alcohol. White crystals are collected and dried and weighed to give 147.0 g of product, mp 174°–176° C.

Substituting 2,6-difluorobenzoyl chloride, 4-ethylbenzoyl chloride, 4-nitrobenzoyl chloride, 4-iodobenzoyl chloride, 2-chloro-4-nitrobenzoyl chloride, 3-bromo-4-toluoyl chloride, 2,5-dichlorobenzoyl chloride or 3,4-(methylene-dioxy) benzoyl chloride or 3,4-naphthoyl chloride or benzoyl chloride in the above reaction yields, respectively. 1-tert-butyl-1,2-bis(2,6-difluorobenzoyl)hydrazine, mp 193°–194° C.; 1-tert-butyl-1,2-bis (p-ethylbenzoyl)hydrazine, mp 178° C.; 1-tert-butyl-1,2-bis (p-nitrobenzoyl)hydrazine, mp>240° C.; 1-tert-butyl-1,2-bis (p-iodobenzoyl)hydrazine, mp>230° C.; 1-tert-butyl-1,2-bis(2-chloro-4-nitrobenzoyl)hydrazine, mp 155°–158° C.; 1-tert-butyl-1,2-bis(3-bromo-p-toluoyl)hydrazine, mp 177°–178° C.; 1-tert-butyl-1,2-bis(2,5-dichlorobenzoyl)hydrazine, mp 198°–200° C.; 1-tert-butyl-1,2-bis[3,4-(methylenedioxy)-benzoyl]hydrazine, mp>235° C.; and 1-tert-butyl-1,2-di-2-naphthoylhydrazine, >235.

These reactions are illustrated below:

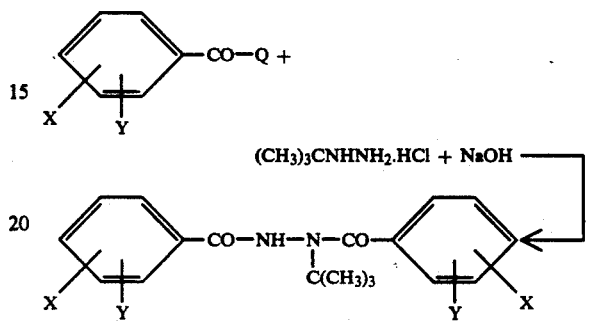

wherein Q is halogen, preferably chlorine and X and Y are each independently hydrogen, halogen, $C_1$–$C_3$ alkyl, methoxy, nitro, $CF_3$ or $R_1CF_2Z$ and when taken together X and Y may form a ring in which XY are represented by the structure $-OCH_2O$, $-OCF_2O$ or

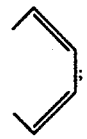

Z is S or O; $R_1$ is H, F, $CHF_2$ or $CF_3$.

EXAMPLE 4

Preparation of 2-benzoyl-1-tert-butyl-1-(3,4-dichlorobenzoyl)hydrazine

Benzoyl-2-tert-butylhydrazine (4.8 g, 0.25 mole) is stirred vigorously in a two-phase system of 50 mL of methylene chloride and 25 mL of 10% aqueous sodium hydroxide (2.5 g, 0.063 mole) until all dissolves. To this solution is added a solution of 3,4-dichlorobenzoyl chloride (7.3 g, 0.025 mole) in methylene chloride. After stirring the two-phase mixture several hours at ambient temperature, the solid is removed and washed with water and methylene chloride. Recrystallization from 2-propanol gives 7.1 g (78%) of product with mp 234°–235° C.

This reaction may be illustrated as follows:

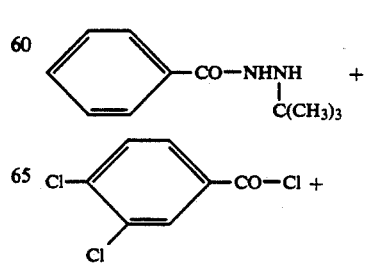

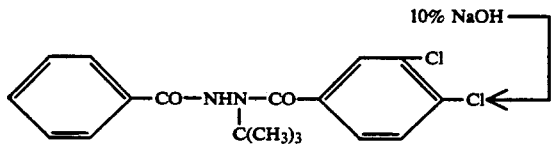

Following the above procedure but substituting the appropriately substituted benzoyl-2-tert-butylhydrazine for benzoyl-2-tert-butylhydrazine and the appropriately substituted benzoylhalide for 3,4-dichlorobenzoyl chloride yields: 2-benzoyl-1-tert-butyl-1-p-toluoyl-hydrazine, mp 194°-195° C.

EXAMPLE 5

Preparation of 1-benzoyl-1-tert-butyl-2-(3,4-dichlorobenzoyl)hydrazine 3,4-Dichlorobenzoyl-2-tert-butylhydrazine (5.63 g, 0.0215 mole) is added to a rapidly stirring mixture of 40 mL of methylene chloride and 20 mL of 10% aqueous sodium hydroxide (2 g, 0.05 mole). Benzoyl chloride (d=1.211, 2.5 mL, 3.03 g, 0.0215 mole) in methylene chloride is added and the reaction mixture stirred vigorously for approximately three hours at ambient temperature. The resulting solid is collected and washed with water and methylene chloride.

The dried product weights 6.18 g with mp 206.5°-208.5° C.

The reaction is illustrated below:

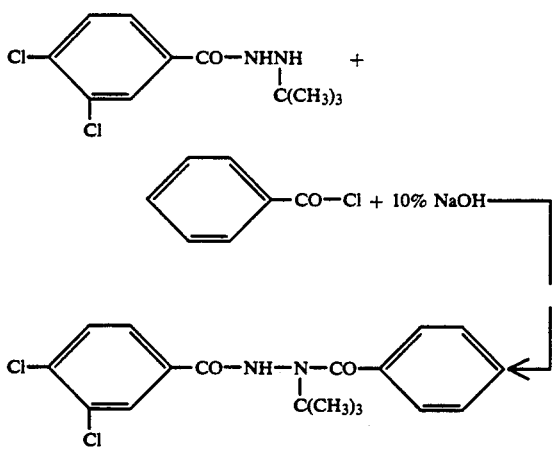

Following the above procedure but substituting the appropriately substituted benzoyl-2-tert-butylhydrazine for 3,4-dichlorobenzoyl-2-tert-butylhydrazine and the appropriately substituted benzoyl chloride for benzoyl chloride yields the following compounds: 1-tert-butyl-2-(p-chlorobenzoyl)-1-p-toluoylhydrazine, mp 223.5°-224.0° C.; 1-p-anisoyl-1-tert-butyl-2-(3,4-dichlorobenzoyl)hydrazine, mp >230° C.; 1-tert-butyl-2-(3,4-dichlorobenzoyl)-1-o-toluoylhydrazine, mp 133°-136° C.; 1-tert-butyl-2-(3,4-dichlorobenzoyl)-1-(p-nitrobenzoyl)hydrazine, mp >230° C.; 1-tertbutyl-2-(3,4-dichlorobenzoyl)-1-(α, α, α-trifluoro-p-toluoyl)hydrazine, mp 212°-213° C.; and 1-tert-butyl-2-(3,4-dichlorobenzoyl-1-(α, α, α-trifluoro-o-toluoyl)hydrazine, mp 171°-172.5° C.

EXAMPLE 6

Preparation of benzoic acid, 3,4-dichloroisopropylidenehydrazine 3,4-Dichlorobenzoic acid hydrazide (11.7 g, 0.060 mole) is placed in the thimble of a Soxhlet extractor and flooded with hot acetone from an attached distillation flask. After overnight reflux, the acetone mixture concentrated under vacuum to afford a white solid. Recrystallization from ethyl acetate petroleum ether gives 9.5 g of the title compound as white crystals, mp 141°-144° C.

This reaction is illustrated as below:

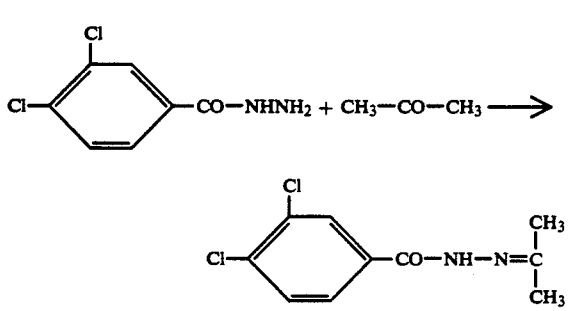

Following the above procedure but substituting the appropriate aldehyde or ketone for acetone yields the following compounds: benzoic acid (1-ethylpropylidene)hydrazide, mp 89°-91° C.; and benzoic acid (2,2-dimethylpropylidene)hydrazide, mp 168°-169° C.

EXAMPLE 7

Preparation of 3,4-dichlorobenzoic acid, 2-isopropylhydrazide 3,4-Dichlorobenzoic acid isopropylidenehydrazide (9.2 g, 0.040 mole) and 100 mg of platinum oxide in 100 mL of methanol in a Parr hydrogenation apparatus is shaken for one hour and 30 minutes under an initial hydrogen pressure of 40 psig. The filtered reaction mixture is concentrated under vacuum and the resulting solids are recrystallized three times from isopropyl alcohol to give 2.6 g of the title compound as a white crystalline product, mp 112.5°-115° C.

The reaction is illustrated below:

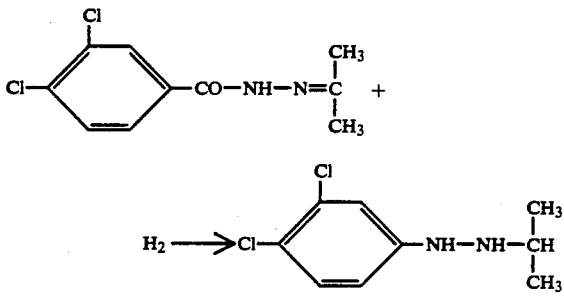

EXAMPLE 8

Preparation of 1-benzoyl-2-(3,4-dichlorobenzoyl)-1-isopropylhydrazine

A mixture of 3,4-dichlorobenzoic acid, 2-isopropylhydrazide (0.98 g, 0.004 mole) and benzoyl chloride (0.56 g, 0.004 mole) is stirred overnight in 1.2 mL of ethylene dichloride and 6.5 mL of 10% sodium hydroxide. The organic phase is removed and the aqueous mixture is extracted with 25 mL of ethylene dichloride. The organic extracts are combined and concentrated to a yellow oil which is taken up in hot isopropyl alcohol. Cooling the alcohol solution causes precipitation of the title compound as a white crystalline product, which is collected by filtration and has a mp of 157° C.

Following one or more of the procedures described in examples 1–8 above yields the compounds listed in Table I below. The reactions is graphically illustrated below.

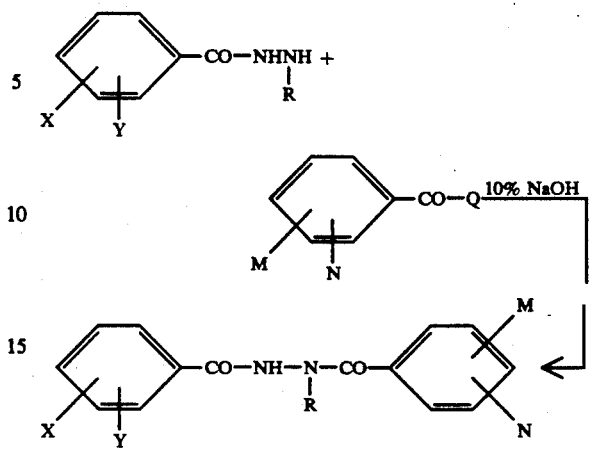

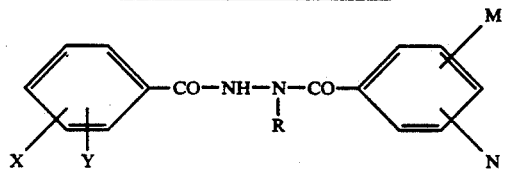

TABLE I

Compounds having the structure

| R | X | Y | M | N | mp °C. |
|---|---|---|---|---|---|
| C(CH₃)₃ | H | 4Cl | H | 4Cl | >240 |
| C(CH₃)₃ | 3Cl | 4Cl | 3Cl | 4Cl | 228.0–229.0 |
| C(CH₃)₃ | 2CH₃ | H | 2CH₃ | H | 196.0–197.0 |
| C(CH₃)₃ | 2Cl | 4Cl | 2Cl | 4Cl | 115.0–117.0 |
| C(CH₃)₃ | H | 4CF₃ | H | 4CF₃ | 226.0–227.0 |
| C(CH₃)₃ | H | 4OCH₃ | H | 4OCH₃ | 119.0–201.0 |
| C(CH₃)₃ | 3Cl | 4Cl | H | H | 206.5–208.5 |
| C(CH₃)₃ | 3Cl | 4Cl | H | 4Cl | >240 |
| C(CH₃)₃ | 3Cl | 4Cl | H | 4CN | 230 |
| C(CH₃)₃ | 3Cl | 4Cl | H | 4OCH₃ | >230 |
| C(CH₃)₃ | —CH=CH—CH=CH— (2,3) | | —CH=CH—CH=CH— (2,3) | | 182.0–183.0 |
| α-naphthyl | | | | | |
| C(CH₃)₃ | 3Cl | 4Cl | 2CH₃ | H | 133.0–136.0 |
| C(CH₃)₃ | 3Cl | 4Cl | H | SO₂CH₃ | 237.0–240.0 |
| CH(CH₃)₂ | 3Cl | 4Cl | 3Cl | 4Cl | 154.0–156.0 |
| C(CH₃)₃ | 4Br | H | 4Br | H | 219.0–220.0 |
| C(CH₃)₃ | H | 4F | H | 4F | 196.0–198.0 |
| C(CH₃)₃ | 3Cl | 4Cl | H | 4NO₂ | >230 |
| C(CH₃)₃ | 3Cl | 4Cl | H | 4CF₃ | 212.0–213.0 |
| C(CH₃)₃ | 3Cl | 4Cl | H | 4CH₃ | 225.5–227.0 |
| C(CH₃)₃ | H | H | 3Cl | 4Cl | 234.0–235.5 |
| C(CH₃)₃ | 3Cl | 4Cl | 2F | 6F | 195.0–197.0 |
| CH(CH₃)₂ | 3Cl | 4Cl | H | H | 163.0–164.5 |
| C(CH₃)₃ | H | 4CH₃ | H | 4CH₃ | 218.0–219.0 |
| C(CH₃)₃ | H | 4Cl | 3Cl | 4Cl | 190.0–192.0 |
| C(CH₃)₃ | 2F | H | 2F | H | 135.0–137.0 |
| C(CH₃)₃ | 3Cl | 4Cl | 2CF₃ | H | 171.0–172.5 |
| C(CH₃)₃ | 3Cl | H | 3Cl | H | 205.0–206.0 |
| C(CH₃)₃ | H | 2Cl | H | 2Cl | 222.0–223.0 |
| C(CH₃)₃ | 2F | 6F | 2F | 6F | 236.0 |
| C(CH₃)₃ | —OCH₂O-(3,4) | | —OCH₂O-(3,4) | | 220.0–221.0 |
| C(CH₃)₃ | 2Cl | 4NO₂ | 2Cl | 4NO₂ | 155.0–158.0 |
| CH(C₂H₅)₂ | H | H | H | H | 199.0–201.0 |
| C(CH₃)₃ | 3Cl | 5Cl | 3Cl | 5Cl | 219.0–221.0 |
| C(CH₃)₃ | H | 2CF₃ | H | 2CF₃ | 211.0 |
| C(CH₃)₃ | H | 3CH₃ | H | 3CH₃ | 152.0–153.0 |
| cyclohexyl | H | H | H | H | 194.0–197.0 |
| n-C₄H₉ | H | H | H | H | 106.0–108.0 |

TABLE I-continued

Compounds having the structure

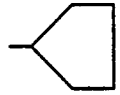

| R | X | Y | M | N | mp °C. |
|---|---|---|---|---|---|
| (cyclopropyl) | H | H | H | H | 185.0–188.0 |
| $C(CH_3)_3$ | —CH=CH—CH=CH— (3,4) | | —CH=CH—CH=CH— (3,4) | | >235 |
| $C(CH_3)_3$ | H | $4C_2H_5$ | H | $4C_2H_5$ | 178.0 |
| $C(CH_3)_3$ | 3Br | $4CH_3$ | 3Br | $4CH_3$ | 177.0–178.0 |
| $C(CH_3)_3$ | 4Cl | H | $4CH_3$ | H | 223.0–224.0 |
| $C(CH_3)_3$ | H | H | $4CH_3$ | H | 194.0–195.0 |
| $C(CH_3)_3$ | H | $4NO_2$ | H | $4NO_2$ | >240.0 |
| $C(CH_3)_3$ | H | 4I | H | 4I | >230.0 |
| $C(CH_3)_3$ | 2Cl | 5Cl | 2Cl | 5Cl | 199.0–200.0 |
| $C(CH_3)_3$ | 2I | H | 2I | H | 206.0–207.0 |
| $C(CH_3)_3$ | 2Cl | H | H | 4F | >250.0 |
| $CH(CH_3)_2$ | H | H | H | H | |

EXAMPLE 9

Preparation of acetone tert-butylhydrazone

To 6.6 g of acetone, cooled in an ice bath, is added 5.0 g of tert-butylhydrazine. The mixture is stirred and then allowed to stand for several minutes. Ether and potassium hydroxide pellets are then added to the mixture. The mixture is stirred, and then the ethereal layer is separated from the mixture. Distillation of the ethereal layer yields the product acetone tert-butylhydrazone b.p. 132°–134° C.

The reaction is illustrated as follows:

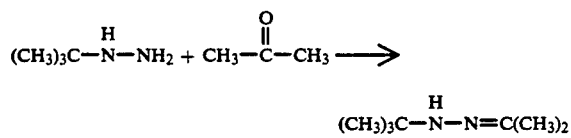

EXAMPLE 10

Preparation of 1-tert-butyl-2-isopropylidenehydrazide of benzoic acid

Acetone tert-butylhydrazone (2.0 g) is admixed with 4.4 g of benzoyl chloride and 15 mL of 10% sodium hydroxide. The mixture is stirred until the benzoyl chloride odor is no longer detectable. The resulting product is then dissolved in ether and dried over magnesium sulfate. Evaporation of the solvent from the mixture leaves acetone N-tert-butyl-N-benzoylhydrazone, b.p. 100°–103° C. This product also is referred to as 1-tert-butyl-2-isopropylidenehydrazide of benzoic acid.

Following the above procedure, but substituting p-chlorobenzoyl chloride for benzoyl chloride yields the product 1-tert-butyl-2-isopropylidenehydrazide of p-chlorobenzoic acid.

Substitution of the o-nitrobenzoyl chloride or o-fluorobenzoyl chloride for benzoyl chloride in the above procedure yields, respectively, 1-tert-butyl-2-isopropylidenehydrazide of o-nitrobenzoic acid and 1-tert-butyl-2-isopropylidenehydrazide of p-fluorobenzoic acid. The reactions are illustrated as follows:

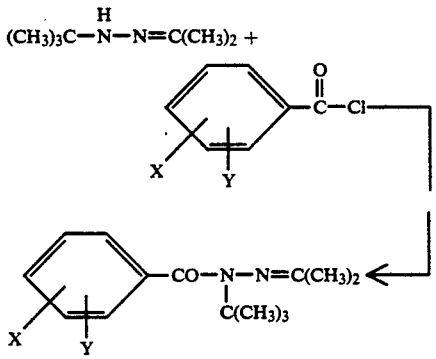

EXAMPLE 11

Preparation of benzoic acid, 1-tert-butylhydrazide

A solution of 0.5 g of the 1-tert-butyl-2-isopropylidenehydrazide of benzoic acid, 3 mL of 10% hydrochloric acid and 3 mL of methanol is mixed and allowed to stand for 12 hours. The mixture is made basic with dilute sodium hydroxide. The methanol is evaporated from the mixture yielding the product 1-tert-butylhydrazide of benzoic acid, m.p. 117°–123° C.

The above procedure is used, but 1-tert-butyl-2-isopropylidenehydrazide of p-chlorobenzoic acid is substituted for 1-tert-butyl-2-isopropylidenehydrazide of benzoic acid. This yields 1-tert-butylhydrazide of p-chlorobenzoic acid, m.p. 134°–136° C.

Similarly, 1-tert-butylhydrazide o-nitrobenzoic acid, m.p. 141°–144° C. and 1-tert-butylhydrazide of p-fluorobenzoic acid, m.p. 136°–137° C.; is prepared by the above reaction using the appropriately substituted benzoic acid, 1-tert-butyl-2-isopropylidenehydrazide. The reactions are illustrated as follows:

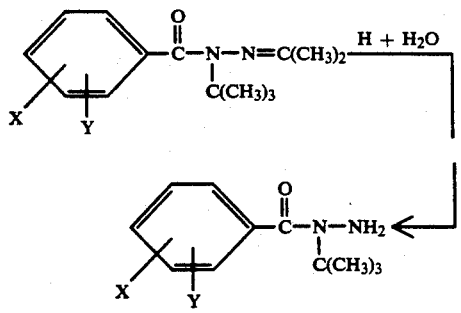

EXAMPLE 12

Insecticidal activity of the compounds of the invention

The compounds of the present invention exhibit insecticidal activity against a variety of insects at various concentrations of active ingredient in acetone-water solutions. As illustrative of this insecticidal activity is control of *Spodoptera eridania* (third-instar larvae, southern armyworm), *Spodoptera eridania* (seven-day residual), *Spodoptera eridania* (third-instar cut-stem systemic test, southern armyworm), *Anopheles quadrimaculatus* (adults, common malaria mosquito), *Heliothis virescens* (third-instar tobacco budworm), *Blattella germanica* (residue test, adult male German cockroach), and *Leptinotarsa decemlineata* (Colorado potato beetles).

Further, systemic activity of the compounds is observed when tested for controlling Colorado potato beetles (*Leptinotarsa decemlineata*) on potato plants, (*Solanum tuberosum*). These beetles are resistant to carbamates, phosphates and pyrethroids but are controlled by the present compounds.

Bean plants, *Phaseolus limensis*, also are protected from southern armyworms, *Spodoptera eridania* and systemically protected from potato leafhoppers, *Empoasca abrupta*.

Maize plants (*Zea mays* L. plants) also are protected from insect attack of southern armyworm larvae (*Spodoptera eridania*, third-instar larvae, southern armyworm) and systemically from southern corn rootworm (*Diabrotical undecimpunctata howardi*).

Rice plants, *Oryza sativa*, are protected via systemic application, as well as by foliar application, from armyworms, *Spodoptera frugiperda*, and leafhoppers, *Empoasca abrupta*.

Cotton plants *Gossypium hirsutum*, also are systemically protected, as well as by foliar application from tobacco budworms (*Heliotris virescens*).

What is claimed is:

1. A compound having the structural formula:

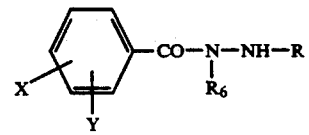

wherein R is hydrogen; $R_6$ is tert-butyl; X and Y are each independently H, $C_1$–$C_3$ alkyl, $C_1$–$C_3$ alkoxy, $C_1$–$C_3$ alkylthio, $C_1$–$C_3$ alkylsulfinyl, $C_1$–$C_3$ alkylsulfonyl, cyano, F, Cl, Br, I, nitro, $CF_3$, $R_1CF_2Z$—, 1,1-difluoro-2,2-dichloroethoxy, $R_2CO$ or $R_3R_4N$; Z is $S(O)_n$ or O; $R_1$ is H, F, $CHF_2$, CHFCl or $CF_3$; $R_2$ is $C_1$–$C_3$ alkyl, $C_1$–$C_3$ alkoxy or $R_3R_4N$; $R_3$ is H or $C_1$–$C_3$ alkyl; $R_4$ is H, $C_1$–$C_3$ alkyl or $R_5CO$; $R_5$ is H or $C_1$–$C_3$ alkyl and n is 0, 1 or 2; with the proviso that at least one of X and Y is a substituent other than hydrogen.

2. The compound according to claim 1, wherein said compound is p-fluorobenzoic acid 1-tert-butylhydrazide.

3. The compound according to claim 1 which is p-chlorobenzoic acid 1-tert-butyl hydrazide.

4. The compound according to claim 1 which is o-nitrobenzoic acid 1-tert-butylhydrazide.

* * * * *